(12) United States Patent
Gupta et al.

(10) Patent No.: US 7,598,073 B2
(45) Date of Patent: Oct. 6, 2009

(54) METHODS FOR PRODUCING HIGH YIELDS OF ZYGOTIC-LIKE COTYLEDONARY PINE EMBRYOS UTILIZING MEDIA THAT INCLUDE A DISACCHARIDE AND GLUCOSE

(75) Inventors: Pramod K. Gupta, Federal Way, WA (US); Diane Gail Holmstrom, Bonney Lake, WA (US); Bonnie Larson, Granite Falls, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 60 days.

(21) Appl. No.: 10/394,549

(22) Filed: Mar. 21, 2003

(65) Prior Publication Data

US 2004/0003426 A1    Jan. 1, 2004

(51) Int. Cl.
*A01H 4/00*  (2006.01)
*A01H 7/00*  (2006.01)

(52) U.S. Cl. .............. 435/240.45; 435/240.4; 435/240.46; 435/240.47; 435/240.49; 435/240.54; 435/172.1

(58) Field of Classification Search .............. 435/6
See application file for complete search history.

(56) References Cited

U.S. PATENT DOCUMENTS

| | | | |
|---|---|---|---|
| 4,217,730 A | 8/1980 | Abo El-Nil | |
| 4,801,545 A | 1/1989 | Stuart et al. | |
| 4,957,866 A | 9/1990 | Gupta et al. | |
| 5,034,326 A | 7/1991 | Pullman et al. | |
| 5,036,007 A * | 7/1991 | Gupta et al. | 435/422 |
| 5,041,382 A | 8/1991 | Gupta et al. | |
| 5,153,130 A | 10/1992 | Kinnersley et al. | |
| 5,183,757 A | 2/1993 | Roberts et al. | |
| 5,187,092 A | 2/1993 | Uddin | |
| 5,236,841 A | 8/1993 | Gupta et al. | |
| 5,238,835 A | 8/1993 | McKersie et al. | |
| 5,294,549 A | 3/1994 | Pullman et al. | |
| 5,413,930 A | 5/1995 | Becwar et al. | |
| 5,464,769 A | 11/1995 | Attree et al. | |
| 5,482,857 A | 1/1996 | Gupta et al. | |
| 5,491,090 A | 2/1996 | Handley, III et al. | |
| 5,501,972 A | 3/1996 | Westcott | |
| 5,506,136 A * | 4/1996 | Becwar et al. | 435/422 |
| 5,523,230 A | 6/1996 | Smith | |
| 5,534,433 A | 7/1996 | Coke | |
| 5,534,434 A | 7/1996 | Coke | |
| 5,563,061 A | 10/1996 | Gupta | |
| 5,564,224 A | 10/1996 | Carlson et al. | |
| 5,565,355 A | 10/1996 | Smith | |
| 5,587,312 A | 12/1996 | van Holst et al. | |
| 5,610,051 A | 3/1997 | Becwar et al. | |
| 5,677,185 A | 10/1997 | Handley, III | |
| 5,731,191 A * | 3/1998 | Rutter et al. | 435/430.1 |
| 5,731,203 A | 3/1998 | Handley, III | |
| 5,731,204 A | 3/1998 | Rutter et al. | |
| 5,821,126 A | 10/1998 | Durzan et al. | |
| 5,840,581 A | 11/1998 | Carraway et al. | |
| 5,850,032 A | 12/1998 | Wann | |
| 5,856,191 A | 1/1999 | Handley, III | |
| 5,985,667 A | 11/1999 | Attree et al. | |
| 6,022,744 A | 2/2000 | Tetteroo et al. | |
| 6,117,678 A | 9/2000 | Carpenter et al. | |
| 6,134,830 A | 10/2000 | Welty | |
| 6,150,167 A | 11/2000 | Carpenter et al. | |
| 6,180,405 B1 | 1/2001 | Aitken-Christie et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,417,001 B2 | 7/2002 | Aitken-Christie et al. | |
| 6,444,467 B1 | 9/2002 | Fan et al. | |
| 6,492,174 B1 | 12/2002 | Pullman et al. | |
| 2002/0012994 A1 | 1/2002 | Aitken-Christie et al. | |
| 2002/0092037 A1 | 7/2002 | Connett-Porceddu et al. | |
| 2002/0100083 A1 | 7/2002 | Connett-Porceddu et al. | |

FOREIGN PATENT DOCUMENTS

| | | |
|---|---|---|
| AU | A-51613/90 A1 | 2/1990 |
| EP | 0 300 730 B1 | 1/1989 |
| EP | 0 618 766 B1 | 10/1994 |
| EP | 0 934 691 A2 | 8/1999 |
| WO | WO 95/33822 A1 | 12/1995 |

(Continued)

OTHER PUBLICATIONS

Lipavska et al. Invited Review: Somatic Embryogenesis in Conifers: The Role of Carbohydrate Metabolism.In Vitro Cell. Dev. Biol. Plant 40 Jan.-Feb. 23-30, 2004.*

(Continued)

*Primary Examiner*—Annette H Para
(74) *Attorney, Agent, or Firm*—Christensen O'Connor Johnson Kindness PLLC

(57) ABSTRACT

The present invention provides methods for producing cotyledonary pine embryos. The methods of the invention each include the step of culturing embryogenic pine tissue in, or on, a medium comprising a disaccharide and glucose to yield cotyledonary pine embryos, wherein the disaccharide and glucose are each present in the medium at a concentration of less than 3 percent. The present invention also provides cotyledonary pine embryos prepared by a method of the invention.

26 Claims, 1 Drawing Sheet

FOREIGN PATENT DOCUMENTS

WO     WO 98/48279 A1    10/1998
WO     WO 01/20972 A1     9/2000

OTHER PUBLICATIONS

Attree, S.M. et al., "Somatic Embryo Maturation, Germination, and Soil Establishment of Plants of Black and White Spruce (*Picea mariana* and *Picea glauca*)," *Can. J. Bot.* 68:2583-2589, 1990.

Attree, S.M., et al., "Initiation of Embryogenic Callus and Suspension Cultures, and Improved Embryo Regeneration of Protoplasts, of White Spruce (*Picea glauca*)," *Can. J. Bot.* 67:1790-1795, 1989.

Attree, S.M., et al., "Plantlet Regeneration From Embryogenic Protoplasts of White Spruce (*Picea glauca*), " *Bio/Technology* 7:1060-1062, 1989.

Bonga, J.M., et al., *Forestry Sciences: Cell and Tissue Culture in Forestry*, vol. 1, *General Principles and Biotechnology*, Martinus Nijhoff Publishers, Netherlands, 1987.

Bonga, J.M., et al., *Forestry Sciences: Cell and Tissue Culture in Forestry*, vol. 2, *Specific Principles and Methods: Growth and Developments*, Martinus Nijhoff Publishers, Netherlands, 1987.

Bonga, J.M., et al., *Forestry Sciences: Cell and Tissue Culture in Foresty*, vol. 3, *Case Histories: Gymnosperms, Angiosperms and Palms*, Martinus Nijhoff Publishers, Netherlands, 1987.

Boulay, M.P., et al., "Development of Somatic Embryos From Cell Suspension Cultures of Norway Spruce (*Picea abies* Karst.)," *Plant Cell Reports* 7:134-137, 1988.

Cornu, D. and C. Geoffrion, "Aspects of Somatic Embryogenesis in Larch Trees," *Bull. Soc. Bot. Fr.*, 137 Actual. Bot. (3/4):25-34, 1990 [translation].

Gupta, P.K., et al., "Scale-Up Somatic Embryogenesis of Conifers For Reforestation," *Proceedings of the 3rd Canadian Workshop on Plant Tissue Culture and Genetic Engineering, University of Guelph, Symposium 1: Somatic Embryogenesis and Synthetic Seeds*, Abstract, Jun. 1992.

Hakman, I. and L.C. Fowke, "An Embryogenic Cell Suspension Culture of *Picea glauca* (White Spruce)," *Plant Cell Reports* 6:20-22, 1987.

Jain, S.M., et al., *Forestry Sciences: Somatic Embryogenesis in Woody Plants*, vol. 3, *Gymnosperms*, Kluwer Academic Publishers, Netherlands, 1995.

Keinonen-Mettälä, K., et al., "Somatic Embryogenesis of *Pinus sylvestris*," *Scand. J. For. Res.* 11:242-250, 1996.

Krogstrup, P. "Somatic Embryogenesis in Sitka Spruce (*Picea sitchensis* (Bong.) Carr.)," *Plant Cell Reports* 7:594-597, 1988.

Lelu, M.A. et al., "Effect of Maturation Duration on Desiccation Tolerance in Hybrid Larch (*Larix X Leptoeuropaea dengler*) Somatic Embryos," In Vitro *Cell. Dev. Biol.* 3115-20, 1995.

Lu, C.-Y. and T.A. Thorpe, "Somatic Embryogenesis and Plantlet Regeneration in Cultured Immature Embryos of *Picea glauca*," *J. Plant Physiol.* 128:297-302, 1987.

Mathur, G. et al., "Studies on Somatic Embryogenesis From Immature Zygotic Embryos of CHIR Pine (*Pinus roxburghii*Sarg.)," *Current Science* 79(7):999-1004, 2000.

Norgaard, J.V., and P. Krogstrup, "Cytokinin Induced Somatic Embryogenesis From Immature Embryos of *Abies nordmanniana* Lk., "*Plant Cell Reports* 9:509-513, 1991.

Roberts, D.R., "Abscisic Acid and Mannitol Promote Early Development, Maturation and Storage Protein Accumulation in Somatic Embryos of Interior Spruce," *Physiologia Plantarum* 83:247-254, 1991.

Roberts, D.R., et al., "Interaction Between Maturation and High Relative Humidity Treatments and Their Effects on Germination of Sitka Spruce Somatic Embryos," *J. Plant Physiol.* 138:1-6, 1991.

Roberts, D.R., et al., "Synchronous and High Frequency Germination of Interior Spruce Somatic Embryos Following Partial Drying at High Relative Humidity," *Can. J. Bot.* 68:1086-1090, 1989.

Thompson, R.G. and P. von Aderkas, "Somatic Embryogenesis and Plant Regeneration From Mature Embryos of Western Larch," *Plant Cell Reports* 11:379-386, 1992.

Timmis, R., "Bioprocessing for Tree Production in the Forest Industry: Conifer Somatic Embryogenesis," *Biotechnol. Prog* 14(1):156-166, 198.

von Aderkas, P., et al., "Charcoal Affects Early Development and Hormonal Concentrations of Somatic Embryos of Hybrid Larch," *Tree Physiology* 22:431-434, 2002.

von Arnold, S. and I. Hakman, "Regulation of Somatic Embryo Development in *Picea abies* by Abscisic Acid (ABA)," *J. Plant Physiol.* 132:164-169, 1988.

von Arnold, S. and T. Eriksson, "A Revised Medium for Growth of Pea Mesophyll Protoplasts," *Physiol.* Plant 39:257-260, 1977.

Webb, D.T., et al., "Factors Influencing the Induction of Embryogenic and Caulogenic Callus From Embros of *Picea glauca* and *P. engelmanii*," *Can. J. For. Res.* 19:1303-1308, 1989.

Lelu, M., et al., "Somatic Embryogenesis and Plantlet Development in *Pinus Sylvestris* and *Pinus Pinaster* on Medium With and Without Growth Regulators," *Physiol. Plant.* 105:719-728, 1999.

Saborio, F., et al., "In Vitro Regeneration of Plantlets from Mature Embryos of *Pinus Ayacahuite*," *Tree Physiol.* 17:787-796, 1997.

Nagmani, R., et al., "Anatomical Comparison of Somatic and Zygotic Embryogeny in Conifers," in S.M. Jain et al. (eds.), vol. 1, Somatic Embryogenesis in Woody Plants, Series: Forestry Sciences, vol. 44, 1995, pp. 23-48.

Lin Xueqin et al: "Culture of isolated zygotic embryos of Pinus radiata D. Don. Part I: Factors influencing in vitro germination and growth of isolated embryos." In Vitro Cellular & Developmental Biology Plant, vol. 38, No. 2, Mar. 2002, pp. 191-197, XP009014300 ISSN: 1054-5476.

Ramarosandratana A et al: "Effects of carbohydrate source, polyethylene glycol and gellan gum concentration on embryonal-suspensor mass (ESM) proliferation and maturation of maritime pine somatic embryos." In Vitro Cellular & Developmental Biology Plant, vol. 37, No. 1, Jan. 2001, pp. 29-34, XP009014337 ISSN: 1054-5476.

Li Xin Y et al: "Polyethylene glycol and maltose enhance somatic embryo maturation in loblolly pine (Pinus taeda L.)." In Vitro Cellular & Developmental Biology Plant, vol. 34, No. 1, Mar. 1998, pp. 22-26, XP009014301 ISSN: 1054-5476.

Lin Xin Y et al: "Polyethylene glycol-promoted development of somatic embryos in loblolly pine (Pinus taeda L.)." In Vitro cellular & Developmental Biology Plant, vol. 33, No. 3, 1997, pp. 184-189, XP009014302 ISSN: 1054-5476.

Salajova Terezia et al: "Initiation of embryogenic tissues and plantlet regeneration from somatic embryos of Pinus nigra Arn." Plant Science (Shannon), vol. 145, No. 1, Jul. 13, 1999, pp. 33-40, XP001153749 ISSN: 0168-9452.

Nagmani, R., et al., "Somatic Embryogenesis in Longleaf Pine (Pinus palustris)," Can. J. For. Res. 23(5):873-876, 1993.

\* cited by examiner

METHODS FOR PRODUCING HIGH YIELDS OF ZYGOTIC-LIKE COTYLEDONARY PINE EMBRYOS UTILIZING MEDIA THAT INCLUDE A DISACCHARIDE AND GLUCOSE

FIELD OF THE INVENTION

The present invention relates to methods for producing plant embryos in vitro, and optionally producing plants from the plant embryos.

BACKGROUND OF THE INVENTION

The demand for pine trees to make wood products continues to increase. One proposed solution to this problem is to identify individual trees that possess desirable characteristics, such as a rapid rate of growth, and produce numerous, genetically identical, clones of the superior trees by somatic cloning. These clones can be cultivated to yield stands, or whole forests, of pine trees that possess the desirable characteristic(s).

One method for cloning pine trees utilizes in vitro treatment of isolated, living, pine tissue under conditions that promote formation of pine embryos, and then whole plants, from the treated tissue. The isolated pine tissue may be cultured in the presence of one or more auxins, and/or cytokinins, to promote formation and multiplication of embryogenic tissue that is then cultured under conditions that promote formation of cotyledonary pine embryos. The embryos may then be germinated to yield pine trees. An example of pine embryogenic tissue are embryonal suspensor masses (ESMs) that can be formed, by tissue culture in vitro, from pine embryos dissected from pine seeds. FIG. 1 shows pine embryonal suspensor masses in liquid culture. FIG. 2 shows a cotyledonary pine embryo formed from ESM (cotyledons are visible at the top of the embryo).

A continuing problem, however, is stimulating efficient formation of cotyledonary pine embryos that are capable of germinating with high frequency to yield pine plants. Preferably the cotyledonary pine embryos, formed in vitro, are morphologically, anatomically and biochemically similar, or identical, to zygotic pine embryos formed, in vivo, in pine seeds. In particular, there is a need for methods for producing, in vitro, greater numbers of zygotic-like cotyledonary pine embryos than are produced by prior art methods. Preferably, the germination frequency and quality of the cotyledonary pine embryos produced by the novel methods should be higher than the germination frequency and quality of cotyledonary pine embryos produced by prior art methods.

SUMMARY OF THE INVENTION

The present invention provides methods for producing cotyledonary pine embryos. The methods of the invention yield greater numbers of zygotic-like cotyledonary pine embryos than are produced by prior art methods. Additionally, the germination frequency and quality of the cotyledonary pine embryos produced by the methods of the invention are higher than the germination frequency and quality of cotyledonary pine embryos produced by prior art methods.

The methods of the invention each include the step of culturing embryogenic pine tissue in, or on, a medium including a disaccharide and glucose to yield cotyledonary pine embryos, wherein the disaccharide and glucose are each present in the medium at a concentration of less than 3 percent (i.e., the disaccharide is present in the medium at a concentration of less than 3 percent, and the glucose is present in the medium at a concentration of less than 3 percent). In some embodiments, the medium includes glucose (present at a concentration of less than 3 percent) and at least two disaccharides, wherein the total concentration of all of the disaccharides in the medium is less than 3 percent. The medium can also include one or more absorbent composition(s). The methods of the invention can further include the step of producing one or more pine trees (e.g., a population of pine trees) from the cotyledonary pine embryos prepared in accordance with the invention.

In the practice of some embodiments of the invention, the embryogenic tissue is sequentially cultured on, or in, a series of at least two media, at least one of which includes a disaccharide and glucose that are each present in the medium at a concentration of less than three percent. The medium that includes a disaccharide and glucose is adapted to promote the development and maturation of cotyledonary embryos from embryogenic tissue.

Thus, in some embodiments, the present invention provides methods for producing cotyledonary pine embryos, the methods each including the steps of: (a) culturing embryogenic pine tissue (such as pine embryonal suspensor masses) on, or in, a maintenance medium; and (b) culturing the embryogenic pine tissue treated in accordance with step (a) on development medium comprising a disaccharide and glucose to form cotyledonary pine embryos, wherein the disaccharide and glucose are each present in the development medium at a concentration of less than 3 percent. The development medium may optionally include an absorbent composition. The methods of this aspect of the invention may optionally include the step of culturing pine tissue on, or in, an initiation medium to yield embryogenic pine tissue, which is then cultured on, or in, a maintenance medium as set forth in step (a).

In another aspect, the present invention provides cotyledonary pine embryos prepared in accordance with a method of the invention.

The methods of the present invention are useful, for example, for preparing cotyledonary pine embryos that can be further characterized, such as by genetic or biochemical means, and/or can be germinated to yield small pine plants that can be grown into mature pine trees, if so desired. Thus, for example, the methods of the invention can be used to produce clones of individual pine trees that possess one or more desirable characteristics, such as a rapid growth rate or improved wood quality. For example, the cotyledonary pine embryos of the invention can be used to produce stands, or forests, of pine trees possessing one or more desirable characteristics, such as a rapid growth rate or improved wood quality. The trees can be utilized to produce wood products.

DETAILED DESCRIPTION OF THE PREFERRED EMBODIMENT

Figure 1:
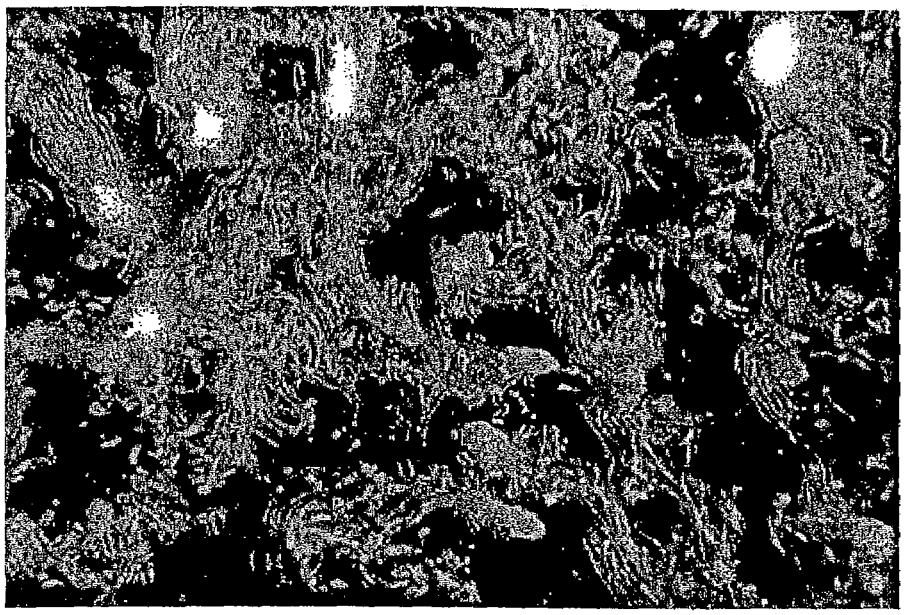
FIG. 1 shows pine embryonal suspensor masses in liquid culture.
Figure 2:
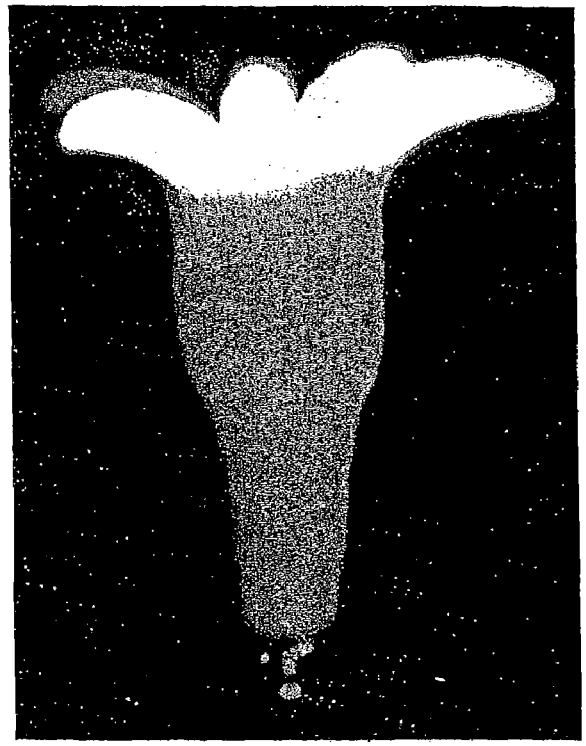
FIG. 2 shows a representative cotyledonary pine embryo prepared using the methods of the invention (cotyledons are visible at the top of the embryo).

Unless specifically defined herein, all terms used herein have the same meaning as they would to one skilled in the art of the present invention.

As used herein, the term "cotyledonary embryo" means an embryo that possesses one or more cotyledons.

The term "disaccharide" refers to carbohydrates that are composed of two monosaccharide residues. Representative examples of disaccharides include maltose, sucrose, lactose, cellobiose, isomaltose, gentiobiose, laminaribiose, chitobiose, xylobiose, inulobiose, mannobiose, hyalobiouronic acid, chondrosine, and cellobiouronic acid.

As used herein, the term "embryogenic tissue" refers to any tissue, derived from a plant of the family Pinacea, that is capable of producing one or more cotyledonary pine embryos when treated in accordance with the methods of the invention. Thus, the term "embryogenic tissue" includes, for example, pine embryonal suspensor masses.

Unless stated otherwise, all concentration values that are expressed as percentages are weight per volume percentages.

In one aspect, the present invention provides methods for producing cotyledonary pine embryos. The methods of the invention each include the step of culturing embryogenic pine tissue in, or on, a medium comprising a disaccharide and glucose to yield cotyledonary pine embryos, wherein the disaccharide and glucose are each present in the medium at a concentration of less than 3 percent.

In some embodiments of the methods of the present invention, at least 50% (such as at least 60%, or such as at least 70%, or such as at least 80%, or such as at least 90%) of the cotyledonary pine embryos produced are zygotic-like (i.e., possess the same morphological features and physiological properties as zygotic cotyledonary pine embryos at the same stage of development). Thus, in some embodiments of the methods of the invention, from 50% to 100% (such as from 60% to 90%, or such as from 70% to 80%) of the cotyledonary pine embryos produced are zygotic-like.

Typically, cotyledonary pine embryos, prepared in accordance with the present invention, each possess one or more of the following characteristics: the embryos are longer (typically by 0.5 mm to 1.0 mm) than embryos that are treated identically except that glucose and/or a disaccharide are not each present in the culture medium at a concentration less than three percent; the embryos each include from eight to twelve cotyledons; and embryos treated in accordance with the present invention develop faster than embryos that are treated identically except that glucose and/or a disaccharide are not each present in the culture medium at a concentration greater than three percent (e.g., in some embodiments, embryos prepared in accordance with the present invention develop within nine weeks).

The methods of the invention can be used to produce cotyledonary embryos of any member of the family Pinacea, such as members of the genus *Pinus*, such as Loblolly pine (*Pinus taeda*).

An example of embryogenic tissue useful in the practice of the present invention is embryonal suspensor masses (ESMs). ESMs can be prepared from precotyledonary embryos removed from pine seed. The seed are typically surface sterilized before removing the precotyledonary embryos which are then cultured on, or in, medium that permits formation of ESMs which include early stage embryos in the process of multiplication by budding and cleavage. The medium may, if desired, include hormones that stimulate multiplication of the early stage embryos. Examples of hormones that can be included in the medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L. An example of a medium useful for culturing pine precotyledonary embryos to induce formation of ESMs is medium $BM_1$ set forth in Example 1 herein.

The methods of the invention each include the step of culturing embryogenic pine tissue in, or on, a medium comprising a disaccharide and glucose to yield cotyledonary pine embryos, wherein the disaccharide and glucose are each present at a concentration of less than 3 percent (such as less than 2.9 percent, or such as less than 2.8 percent, or such as less than 2.7 percent, or such as less than 2.6 percent). In some embodiments of the methods of the invention, the disaccharide and glucose are each present in the medium at a concentration of from 1 percent to 2.5 percent. In some embodiments of the methods of the invention, the disaccharide and glucose are each present in the medium at a concentration of from 2 percent to 2.5 percent. In some embodiments of the methods of the invention, the disaccharide is present in the medium at a concentration of 2.5%, and the glucose is present in the medium at a concentration of 1%. In some embodiments of the methods of the invention, the medium includes glucose and at least two disaccharides, wherein the concentration of glucose in the medium is less than 3 percent, and the total concentration of all of the disaccharides in the medium is from 1 percent to 2.5 percent. In some embodiments of the methods of the invention, the medium includes glucose and at least two disaccharides, wherein the glucose is present in the medium at a concentration of less than 3 percent, and the total concentration of all of the disaccharides present in the medium is from 2 percent to 2.5 percent.

In some embodiments of the methods of the invention, embryogenic pine tissue is cultured in, or on, a medium including a disaccharide and glucose, each at a concentration of less than 3 percent, for a period of from six weeks to twelve weeks, such as from eight weeks to twelve weeks, or such as from nine weeks to eleven weeks. In some embodiments of the methods of the invention, embryogenic pine tissue is cultured in, or on, a medium including a disaccharide and glucose, each at a concentration of less than 3 percent, at a temperature of from 20° C. to 24° C., such as from 21° C. to 24° C.

The medium that includes a disaccharide and glucose also may include nutrients (e.g., salts) that sustain the incubated plant tissue, and one or more agents for adjusting the osmolality of the medium to within a desired range. For example, the osmolality of the medium may be from 250 mM/Kg to 450 mM/Kg, such as from 250 mM/Kg to 350 mM/Kg. The pH of the medium can also be adjusted to a desired value. For example, the pH of the medium may be from 4.5 to 6.5, such as from 5.0 to 6.0.

The medium including a disaccharide and glucose can be a liquid medium or a solid medium. When a liquid medium is utilized, the embryogenic tissue is typically placed on an absorbent support (e.g., filter paper) that is soaked in the liquid medium. When a solid medium is utilized, the embryogenic tissue may be placed on the surface of the medium, and may partially penetrate the surface of the solid medium. Thus, solid media include media that are partially solidified and permit the embryogenic tissue to substantially penetrate into the body of the medium, and also include fully solidified media that do not permit the embryogenic tissue to penetrate the body of the solidified medium. Liquid media can be completely or partially solidified by addition of an appropriate amount of a gellant, such as agar or gelrite.

It has been found that the inclusion of an absorbent composition in the medium, that includes a disaccharide and glucose, further promotes production of a high yield of cotyledonary pine embryos having improved germination frequency and quality. The absorbent composition can be any composition that is not toxic to the embryogenic tissue at the concentrations utilized in the practice of the present methods, and that is capable of absorbing growth-promoting hormones, and toxic compounds produced by the plant cells during embryo development, that are present in the medium. Thus, the absorbed hormone(s) is/are no longer available to promote the growth of the embryogenic tissue in, or on, the medium, and the absorbed toxins cannot adversely affect the plant cells. In this context, the term "absorbing" encompasses any chemical or physical interaction between the absorbent composition and one or more growth-promoting hormones, and/or toxins, in the medium, so that the growth-promoting hormone(s), and/or toxins, are bound to the absorbent composition.

Thus, in some embodiments of the methods of the invention, the embryogenic tissue is incubated in, or on, a medium that includes growth-promoting hormones, such as auxins and/or cytokinins, to promote multiplication of the embryogenic tissue. When sufficient embryogenic tissue has been obtained, the embryogenic tissue may then be transferred to medium that does not include growth-promoting hormones, but includes a disaccharide and glucose and, optionally, one or more absorbent compositions. The absorbent composition(s) bind growth-promoting hormones present in the medium so that the rate of multiplication of the embryogenic tissue is reduced, or multiplication is stopped entirely, and the disaccharide and glucose induce production of pine cotyledonary embryos from the embryogenic tissue.

Non-limiting examples of useful absorbent compositions include activated charcoal, soluble poly(vinyl pyrrolidone), insoluble poly(vinyl pyrrolidone), activated alumina, and silica gel. The absorbent composition may be present in an amount, for example, of from 0.01 g/L to 5 g/L. In some embodiments, the absorbent composition is present in an amount of from 0.05 g/L to 1 g/L. In those embodiments of the methods of the invention in which more than one absorbent composition (e.g., at least two absorbent compositions) are present in the medium, the foregoing concentration ranges refer to the total absorbent composition concentration in the medium.

In the practice of some embodiments of the invention, the embryogenic tissue is sequentially cultured on, or in, a series of at least two media, at least one of which includes a disaccharide and glucose that are each present in the medium at a concentration of less than three percent. The medium that includes a disaccharide and glucose is adapted to promote the development and maturation of cotyledonary embryos from embryogenic tissue, such as embryogenic tissue that has been treated with one or more growth hormones. The cotyledonary pine embryos have improved germination frequency and quality.

For example, in the practice of some embodiments of the methods of the invention, embryogenic pine tissue (such as ESM) is cultured on, or in, a maintenance medium that is adapted to promote cell division and growth of the embryogenic tissue. The maintenance medium can be a solid medium, or a liquid medium which can be agitated to promote growth and multiplication of the embryogenic tissue therein. The maintenance medium may contain nutrients that sustain the embryogenic tissue, and may include hormones, such as one or more auxins (e.g., 2,4-D) and/or cytokinins (e.g., kinetin, BAP), that promote cell division and growth of the embryogenic tissue. If auxin is utilized, the concentration of auxin within the maintenance medium can be, for example, from 0.1 mg/L to 10 mg/L (such as from 0.1 mg/L to 5 mg/L). If more than one auxin is present in the medium, the foregoing concentration ranges refer to the total auxin concentration in the medium. If cytokinin is utilized, the concentration of cytokinin within the maintenance medium can be, for example, from 0.1 mg/L to 2 mg/L (such as from 0.1 mg/L to 1 mg/L). If more than one cytokinin is present in the medium, the foregoing concentration ranges refer to the total cytokinin concentration in the medium.

It is generally desirable, though not essential, to include maltose as the sole or principal sugar source in the maintenance medium. The maltose may be present at a concentration of from 0.5 mg/L to 6 mg/L, such as from 1 mg/L to 3 mg/L.

The osmolality of the maintenance medium can be adjusted to a value that falls within a desired range, such as from 100 mM/Kg to 250 mM/Kg, or such as from 100 mM/Kg to 200 mM/Kg. The pH of the maintenance medium may also be adjusted to a value within a desired range, such as from 4.5 to 6.5, or such as from 5.0 to 6.0. The embryogenic tissue is typically incubated in, or on, the maintenance medium at a temperature in the range of from 20° C. to 24° C., such as from 21° C. to 24° C. An example of a suitable maintenance medium is medium $BM_2$ set forth in Example 1 herein.

The embryogenic tissue is incubated in, or on, the maintenance medium until the embryogenic tissue has multiplied by a desired amount (as determined, for example, by the mass of the cultured embryogenic tissue). The embryogenic tissue can then be transferred to a development medium adapted to promote development of high quality cotyledonary pine embryos. The development medium is typically a solid medium, although the development medium can be a liquid medium.

The development medium includes a disaccharide and glucose which are each present at a concentration of less than three percent (such as less than 2.9 percent, or less than 2.8 percent, or less than 2.7 percent, or less than 2.6 percent). In some embodiments, the disaccharide and glucose are each present in the development medium at a concentration of from 1 percent to 2.5 percent. In some embodiments, the disaccharide and glucose are each present in the development medium at a concentration of from 2 percent to 2.5 percent.

The development medium may contain nutrients (e.g., salts) that sustain the embryogenic tissue. Suitable development media typically do not include growth-promoting hormones, such as auxins and cytokinins, but may include the hormone abscisic acid. When abscisic acid is utilized in the development medium, it is typically utilized at a concentration in the range of from 1 mg/L to 200 mg/L, such as from 1 mg/L to 100 mg/L. The osmolality of the development medium can be adjusted to a value that falls within a desired range, such as from 250 mM/Kg to 450 mM/Kg, or such as from 250 mM/Kg to 350 mM/Kg. The pH of the development medium may also be adjusted to a value within a desired range, such as from 4.5 to 6.5, or such as from 5.0 to 6.0. The embryogenic tissue is typically incubated in, or on, the development medium at a temperature in the range of from 20° C. to 24° C., such as from 21° C. to 24° C. An example of a suitable development medium is medium $BM_3$ set forth in Example 1 herein.

In some embodiments of the methods of the invention, embryogenic tissue is incubated in, or on, the development medium for a period of from six weeks to twelve weeks, such as from six weeks to nine weeks.

Thus, in some embodiments, the present invention provides methods for producing cotyledonary pine embryos, the methods each including the steps of: (a) culturing embryogenic pine tissue (such as pine embryonal suspensor masses) on, or in, a maintenance medium; and (b) culturing the embryogenic pine tissue treated in accordance with step (a) on, or in, a development medium comprising a disaccharide and glucose to form cotyledonary pine embryos, wherein the disaccharide and glucose are each present in the development medium at a concentration of less than 3 percent. The development medium may optionally include an absorbent composition. The methods of this aspect of the invention may optionally include the step of culturing pine tissue in, or on, an initiation medium to yield embryogenic pine tissue, which is then cultured in, or on, a maintenance medium as set forth in step (a).

In other embodiments, the present invention provides methods for producing cotyledonary pine embryos, the methods each including the steps of: (a) culturing embryogenic pine tissue (such as pine embryonal suspensor masses) on solid maintenance medium; (b) culturing the embryogenic pine tissue treated in accordance with step (a) in liquid maintenance medium; and (c) culturing the embryogenic pine tissue treated in accordance with step (b) on solid development medium comprising a disaccharide and glucose, to form cotyledonary pine embryos, wherein the disaccharide and glucose are each present in the development medium at a concentration of less than 3 percent. The development medium may optionally include an absorbent composition. The methods of this aspect of the invention may optionally include the step of culturing pine tissue in an initiation medium to yield embryogenic pine tissue, which is then cultured on a maintenance medium as set forth in step (a).

The cotyledonary pine embryos produced using the methods of the invention can optionally be germinated to form small pine plants which can be grown into pine trees, if desired. The cotyledonary pine embryos can be germinated on a solid germination medium, such as medium $BM_5$ medium set forth in Example 1 herein. The germinated plants can be transferred to soil for further growth. For example, the germinated plants can be planted in soil in a greenhouse and allowed to grow before being transplanted to an outdoor site. Typically, the cotyledonary pine embryos are illuminated to stimulate germination. Typically, all the steps of the methods of the invention, except germination, are conducted in the dark.

The methods of the invention can be used, for example, to produce clones of individual pine trees that possess one or more desirable characteristics, such as a rapid growth rate. Thus, in one aspect, the present invention provides methods for producing genetically-identical, cotyledonary pine embryos. The methods of this aspect of the invention each include the step of culturing genetically-identical embryogenic pine tissue in, or on, a medium including a disaccharide and glucose to yield genetically-identical, cotyledonary pine embryos, wherein the disaccharide and glucose are each present in the medium at a concentration of less than 3 percent.

In another aspect, the present invention provides populations of zygotic-like cotyledonary pine embryos. In some embodiments, at least 50% (such as at least 60%, or such as at least 70%, or such as at least 80%, or such as at least 90%) of the cotyledonary pine embryos in the population of cotyledonary pine embryos are zygotic-like. Thus, in some embodiments of this aspect of the invention, from 50% to 100% (such as from 60% to 80%, or such as from 70% to 80%) of the cotyledonary pine embryos in the population of cotyledonary pine embryos are zygotic-like. The methods of the invention can be used to produce the populations of zygotic-like cotyledonary pine embryos of the invention. Thus, in one aspect, the present invention provides populations of pine cotyledonary embryos prepared by a method of the invention.

The following examples merely illustrate the best mode now contemplated for practicing the invention, but should not be construed to limit the invention.

EXAMPLE 1

This Example shows a representative method of the invention for producing a population of Loblolly pine (*Pinus taeda*), cotyledonary embryos, and germination of the embryos.

Female gametophytes containing zygotic embryos are removed from seeds four to five weeks after fertilization. The seed coats are removed but the embryos are not further dissected out of the surrounding gametophyte other than to excise the nucellar end. The cones are stored at 4° C. until used. Immediately before removal of the immature embryos the seeds are sterilized utilizing an initial washing and detergent treatment followed by a ten minute sterilization in 15% $H_2O_2$. The explants are thoroughly washed with sterile distilled water after each treatment.

Table 1 sets forth the compositions of representative media useful for loblolly pine embryogenesis.

TABLE 1

Loblolly Pine Media Compositions

| | BM | BM 1 | BM 2 | BM 3 | BM 4 | BM 5 | BM 6 | BM 7 |
|---|---|---|---|---|---|---|---|---|
| Salts (mg/L) | | | | | | | | |
| $NH_4NO_3$ | 150 | 150 | 150 | 150 | 150 | 206.25 | 150 | 150 |
| $KNO_3$ | 909.9 | 909.9 | 909.9 | 909.9 | 909.9 | 1170 | 909.9 | 909.9 |
| $Ca(NO_3)_2 \cdot 4H_2O$ | 236.15 | 236.15 | 236.15 | 236.15 | 236.15 | | 236.15 | 236.15 |
| $MgSO_4 \cdot 7H_2O$ | 246.5 | 246.5 | 246.5 | 246.5 | 246.5 | 185 | 246.5 | 246.5 |
| $Mg(NO_3)_2 \cdot 6H_2O$ | 256.5 | 256.5 | 256.5 | 256.5 | 256.5 | | 256.5 | 256.5 |
| $MgCl_2 \cdot 6H_2O$ | 50 | 50 | 50 | 50 | 50 | | 50 | 50 |
| $KH_2PO_4$ | 136 | 136 | 136 | 136 | 136 | 85 | 136 | 136 |
| $CaCl_2 \cdot 2H_2O$ | 50 | 50 | 50 | 50 | 50 | 220 | 50 | 50 |
| KI | 4.15 | 4.15 | 4.15 | 4.15 | 4.15 | 0.415 | 4.15 | 4.15 |
| $H_3BO_3$ | 15.5 | 15.5 | 15.5 | 15.5 | 15.5 | 3.1 | 15.5 | 15.5 |
| $MnSO_4 \cdot H_2O$ | 10.5 | 10.5 | 10.5 | 10.5 | 10.5 | 8.45 | 10.5 | 10.5 |
| $ZnSO_4 \cdot 7H_2O$ | 14.4 | 14.4 | 14.4 | 14.4 | 14.4 | 4.3 | 14.4 | 14.4 |
| $Na_2MoO_4 \cdot 2H_2O$ | 0.125 | 0.125 | 0.125 | 0.125 | 0.125 | 0.125 | 0.125 | 0.125 |
| $CuSO_4 \cdot 5H_2O$ | 0.125 | 0.125 | 0.125 | 0.125 | 0.125 | 0.0125 | 0.125 | 0.125 |
| $CoCl_2 \cdot 6H_2O$ | 0.125 | 0.125 | 0.125 | 0.125 | 0.125 | 0.0125 | 0.125 | 0.125 |
| $FeSO_4 \cdot 7H_2O$ | 27.87 | 27.87 | 27.87 | 13.93 | 13.93 | 13.93 | 13.93 | 13.93 |

TABLE 1-continued

Loblolly Pine Media Compositions

|  | BM | BM 1 | BM 2 | BM 3 | BM 4 | BM 5 | BM 6 | BM 7 |
|---|---|---|---|---|---|---|---|---|
| $Na_2EDTA$ | 37.26 | 37.26 | 37.26 | 18.63 | 18.63 | 18.63 | 18.63 | 18.63 |
| Vitamins/Amino Acids | | | | | | | | |
| Nicotinic Acid | 0.5 | 0.5 | 0.5 | 0.5 | 0.5 | 0.5 | 0.5 | 0.5 |
| Pyridoxine HCl | 0.5 | 0.5 | 0.5 | 0.5 | 0.5 | 0.5 | 0.5 | 0.5 |
| Thiamine HCl | 1 | 1 | 1 | 1 | 1 | 1 | 1 | 1 |
| Glycine | 2 | 2 | 2 | 2 | 2 | 2 | 2 | 2 |
| L-proline | | | | 100 | 100 | | 100 | 100 |
| L-asparagine | | | | 100 | 100 | | 100 | 100 |
| L-argenine | | | | 50 | 50 | | 50 | 50 |
| L-alanine | | | | 20 | 20 | | 20 | 20 |
| L-serine | | | | 20 | 20 | | 20 | 20 |
| PEG 8000 mw | | | | 10000 | 13000 | | | |
| Sugar/Agar mg/L | | | | | | | | |
| Myo-Inositol | 200 | 200 | 200 | 1000 | 1000 | 100 | 1000 | 1000 |
| Casein hydrolysate | 500 | 500 | 500 | 500 | 500 | | 500 | 500 |
| L-glutamine | 1000 | 1000 | 1000 | 1000 | 1000 | | 1000 | 1000 |
| Sucrose | | | | | | 20000 | | |
| Maltose | 30 | 30 | 30 | 25000 | 20000 | | 20000 | 20000 |
| Glucose | | | | 10000 | | | | |
| GELRITE | | | | 2500 | 2500 | | | |
| TC Agar | | | | | | 8000 | | |
| Activated carbon | | | | 1000 | 1000 | 2500 | | 1000 |
| Hormones mg/L | | | | | | | | |
| ABA | | | | 25 | 25 | | 10 | |
| 2,4-D | | 11.0 | 1.1 | | | | | |
| BAP | | 1.0 | 0.1 | | | | | |
| Kinetin | | 1.0 | 0.1 | | | | | |

Stage 1—Induction: Sterile gametophytes with intact embryos are placed on a solid $BM_1$ culture medium and held in an environment at 22° C.-25 C. with a 24 hour dark photoperiod for a time of 3-5 weeks. The length of time depends on the particular genotype being cultured. At the end of this time a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 170 mM/kg. Normally it is about 160 mM/kg or even lower (such as 150 mM/kg).

Stage II—Maintenance and Multiplication: Early stage embryos removed from the masses generated in the induction stage are first placed on a $BM_2$ gelled maintenance and multiplication medium. This differs from the induction medium in that the growth hormones (both auxins and cytokinins) are reduced by at least a full order of magnitude. Osmolality of this medium is typically raised from that of the induction medium to about 180 mM/kg or higher by increasing the concentration of myo-inositol to 0.5% w/v. The temperature and photoperiod are again 22°-25 C. with 24 hours in the dark. Embryos are cultured 12-14 days on the $BM_2$ solid medium before transferring to a liquid medium for further subculturing. This liquid medium is of similar composition but lacks the gellant. The embryos at the end of the solid maintenance stage are typically similar in appearance to those from Stage I. After 5 to 6 weekly subcultures on the liquid maintenance medium advanced early stage embryos form. These are characterized by smooth embryonal heads, estimated to typically have over 100 individual cells, with multiple suspensors.

Osmotic potential of the maintenance media typically falls within the range of about 180-400 mM/kg for *Pinus taeda*. Most typically osmotic potential of the maintenance media is in the neighborhood of about 1.5 times higher than that of the induction or multiplication media.

Stage III—Embryo Development: The advanced early stage embryos from Stage II culture are transferred to a filter paper support placed on a pad saturated with liquid development medium. This medium either lacks growth hormones entirely, or has them present only at very low levels and has the same lower level of osmoticants as Stages I and TI. Maltose and glucose are present. Abscisic acid may be included to facilitate further development. An absorbent composition (such as activated charcoal, soluble and insoluble forms of poly(vinyl pyrrolidone), activated alumina, and silica gel) may also be included, such as at a concentration of about 0.1-5 g/L, or about 0.25-2.5 g/L.

The osmotic potential of this medium may be raised substantially over that of the maintenance medium. For example, the osmolality may be as high as 350 mM/kg or even higher. Development is preferably carried out in complete darkness at a temperature of 22°-25 C. until elongated cotyledonary embryos have developed. Development time is typically several weeks, such as 6 to 9 weeks.

Embryos are then incubated at 4° C. to 10° C. for 3 to 4 weeks in a medium that does not include PEG or ABA (e.g., medium BM7).

Stage IV—Drying: The embryos still on their filter paper support are lifted from the pad and placed in a closed container over a saturated solution of $K_2SO_4$, or water, at a relative humidity of 97%, for a period of about three weeks.

Stage V—Germination: The dried cotyledonary embryos from Stage IV are rehydrated by placing them, while still on the filter paper support, for about 24 hours on a pad saturated with liquid germination medium. The embryos are then placed individually on solid BM$_5$ medium for germination. This is a basal medium lacking growth hormones which has been modified by reducing sucrose, myo-inositol and organic nitrogen. The embryos are incubated on BM$_5$ medium for about 6-8 weeks under environmental conditions of 23°-25° C., and a 16 hour light—8 hour dark photoperiod, until the resulting plantlets have a well developed radicle and hypocotyl and green cotyledonary structure and epicotyl. If desired, the cotyledonary embryos may be made into artificial seeds.

Because of the reduced carbohydrate concentration, the osmotic potential of the germination medium is further reduced below that of the development medium. It is normally below about 150 mM/kg (such as about 100 mM/kg).

Stage VI—Conversion: Plantlets from Stage V are removed from the germination medium and planted in a soil comprising equal parts of peat and fine perlite.

EXAMPLE 2

This Example shows the effect on embryo development and germination frequency of culturing Loblolly pine somatic embryos on development medium that includes a combination of 2.5% maltose and 1% glucose.

Three Loblolly pine genotypes were tested: Genotype A, Genotype B, and Genotype C. Embryonal Suspensor Masses (ESM) of each genotype were grown in a flask containing one liter of medium BM2. Each flask of ESM was settled for 15 minutes, the medium was aspirated, and the settled cells were transferred to a new vessel. An equal volume of medium BM6 was added to the cells which were then allowed to settle for 10 minutes. One half of the BM6 medium was removed, and 1.5 ml aliquots of the settled cells (a cell to BM6 ratio of 1:0.5) were transferred directly to development media BM3 (includes glucose and maltose) and BM4 (includes maltose, but not glucose), and also to media BM2, BM5, BM6, and BM7.

After incubation for 4 weeks on the development media, it was observed that medium BM3 promoted faster development than medium BM4. The other media showed no difference from the control medium. After incubation for 12 weeks on the development media, the embryos cultured on the BM3 medium were much larger, longer, and more like zygotic embryos, than the embryos cultured on BM4 medium. The embryos cultured on BM3 medium began developing cotyledons after eight weeks. The embryos cultured on BM3 medium had 8-10 cotyledons (genotype A produced some embryos having 14-16 cotyledons), as compared to 4-6 cotyledons on embryos cultured on BM4 medium. Thus, culturing the embryos on a development medium including maltose and glucose (medium BM3) yielded larger, better quality embryos, with more cotyledons and visible domes, than the other media. Table 2 shows the number of zygotic-like Loblolly pine embryos produced on media BM4 and BM3.

TABLE 2

| Genotype | Medium BM4 | Medium BM3 |
|---|---|---|
| A | 47 | 61 |
| B | 75 | 84 |
| C | 43 | 56 |
| average | 55 | 67 |

Zygotic-like embryos were selected from BM3 and BM4 plates and transferred to a Petri plate containing a filter paper on a pad saturated with medium BM7. The Petri plates were sealed with parafilm and stored in the cold. After 4 weeks, the filter papers with embryos were transferred to mesh bridges in Magenta boxes that contained about 100 ml of water. After 3 weeks of drying in the boxes, the filter papers with embryos were transferred to Petri plates containing a pad saturated with liquid BM5 medium. After 24 hours, the embryos were transferred to solid BM5 medium in germination boxes. The boxes were left in the dark for one week and then transferred to the light room.

Embryos produced on BM3 had a germination frequency that was almost double the germination frequency of embryos produced on BM4. Moreover, the quality of the germinants produced from medium BM3 was better than the quality of the germinants produced from medium BM4. For example, for Genotypes A and B, the bipolar germinants from medium BM3 had straight and thick hypocotyls, and vigorous epicotyl growth. In contrast, bipolar germinants produced from medium BM4 had curved, relatively thin hypocotyls.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for producing cotyledonary pine embryos, said method comprising the steps of:
    (a) culturing embryogenic pine tissue in, or on, a maintenance medium comprising maltose as the sole source of sugar to promote multiplication of the embryogenic tissue; and
    (b) culturing the embryogenic pine tissue multiplied in accordance with step (a) in, or on, a development medium comprising maltose and glucose to yield cotyledonary pine embryos, wherein said maltose is present in the development medium at a concentration of 2.5% and said glucose is present in the development medium at a concentration of 1%.

2. The method of claim 1 wherein the embryogenic pine tissue comprises embryonal suspensor masses.

3. The method of claim 1 wherein at least 60% of the cotyledonary pine embryos comprise from 6 to 12 cotyledons.

4. The method of claim 1 wherein at least 70% of the cotyledonary pine embryos comprise from 6 to 12 cotyledons.

5. The method of claim 1 wherein at least 80% of the cotyledonary pine embryos comprise from 6 to 12 cotyledons.

6. The method of claim 1 wherein at least 90% of the cotyledonary pine embryos comprise from 6 to 12 cotyledons.

7. The method of claim 1 wherein the embryogenic pine tissue is cultured in, or on, the development medium for a period of from six weeks to twelve weeks.

8. The method of claim 1 wherein the embryogenic pine tissue is cultured in, or on, the development medium for a period of from eight weeks to twelve weeks.

9. The method of claim 1 wherein the embryogenic pine tissue is cultured in, or on, the development medium for a period of from nine weeks to eleven weeks.

10. The method of claim 1 wherein the osmolality of the development medium is from 250 mM/Kg to 450 mM/Kg.

11. The method of claim 1 wherein the pH of the development medium comprising maltose and glucose is from 4.5 to 6.5.

12. The method of claim 1 wherein the development medium further comprises an absorbent composition selected from the group consisting of activated charcoal, soluble poly(vinyl pyrrolidone), insoluble poly(vinyl pyrrolidone), activated alumina, and silica gel.

13. The method of claim 12 wherein the absorbent composition is activated charcoal.

14. The method of claim 12 wherein the concentration of the absorbent composition is from 0.01 g/L to 5 g/L.

15. The method of claim 12 wherein the concentration of the absorbent composition is from 0.05 g/L to 1 g/L.

16. The method of claim 1 wherein the development medium further comprises at least two adsorbent compositions, wherein the total concentration of the absorbent composition in the development medium is from 0.01 g/L to 5 g/L.

17. The method of claim 1 wherein the development medium further comprises at least two adsorbent compositions, wherein the total concentration of the absorbent composition in the development medium is from 0.05 g/L to 5 g/L.

18. The method of claim 1 wherein cotyledonary Loblolly pine embryos are produced from Loblolly pine embryogenic tissue.

19. The method of claim 1 wherein the development medium is a liquid medium.

20. The method of claim 1 wherein the development medium is a solid medium.

21. A method for producing cotyledonary pine embryos, said method comprising the steps of:

(a) culturing embryogenic pine tissue in, or on, a maintenance medium comprising maltose as the sole source of sugar to promote multiplication of the embryogenic tissue; and (b) culturing the embryogenic pine tissue multiplied in accordance with step (a) in, or on, a development medium comprising abscisic acid, an absorbent composition, PEG, maltose, and glucose to form cotyledonary pine embryos, wherein said maltose is present in the development medium at a concentration of 2.5%, said glucose is present in the development medium at a concentration of 1%.

22. A population of cotyledonary pine embryos produced by the method of claim 1, wherein at least 50% of the embryos are zygotic-like.

23. A population of cotyledonary pine embryos produced by the method of claim 1 wherein at least 60% of the embryos are zygotic-like.

24. A population of cotyledonary pine embryos produced by the method of claim 1 wherein at least 70% of the embryos are zygotic-like.

25. A population of cotyledonary pine embryos produced by the method of claim 1 wherein at least 80% of the embryos are zygotic-like.

26. A population of cotyledonary pine embryos produced by the method of claim 1 wherein at least 90% of the embryos are zygotic-like.

* * * * *